US010295474B2

United States Patent
Waldie

(10) Patent No.: US 10,295,474 B2
(45) Date of Patent: May 21, 2019

(54) INSPECTION SYSTEM COMPRISING A WIRING HARNESS THAT WHEN CONNECTED TO AN EXTERNAL POWER SUPPLY FOR SUPPLYING ELECTRIC POWER AND IMAGE DATA TO AND FROM AN IMAGING DEVICE MOUNTED WITHIN AN INSPECTED STRUCTURE

(71) Applicant: BAE Systems Australia Limited, Edinburgh, South Australia (AU)

(72) Inventor: James Murray Andrew Waldie, Victoria (AU)

(73) Assignee: BAE SYSTEMS AUSTRALIA LIMITED, Edinburgh (AU)

( * ) Notice: Subject to any disclaimer, the term of this patent is extended or adjusted under 35 U.S.C. 154(b) by 92 days.

(21) Appl. No.: 15/551,150

(22) PCT Filed: Jan. 29, 2016

(86) PCT No.: PCT/AU2016/050050
§ 371 (c)(1),
(2) Date: Aug. 15, 2017

(87) PCT Pub. No.: WO2016/134412
PCT Pub. Date: Sep. 1, 2016

(65) Prior Publication Data
US 2018/0031488 A1    Feb. 1, 2018

(30) Foreign Application Priority Data

Feb. 23, 2015   (AU) ................. 2015900630

(51) Int. Cl.
*B64F 5/60*   (2017.01)
*G01N 21/88*   (2006.01)
(Continued)

(52) U.S. Cl.
CPC ............... *G01N 21/88* (2013.01); *B64F 5/60* (2017.01); *G01J 1/4228* (2013.01); *G01J 1/44* (2013.01);
(Continued)

(58) Field of Classification Search
CPC ........ B64F 5/60; G01N 21/88; G01N 21/954; H04N 7/181
(Continued)

(56) References Cited

U.S. PATENT DOCUMENTS 3,329,074 A    7/1967   Gosselin
3,778,170 A    12/1973  Howell et al.
(Continued)

FOREIGN PATENT DOCUMENTS

DE   202009015603 U1   4/2010
EP       2690761 A1    1/2014
EP       2818908 A1    12/2014

OTHER PUBLICATIONS

International Search Report and Written Opinion of International Application No. PCT/AU2016/050050, dated Mar. 10, 2016, 9 pages.
(Continued)

*Primary Examiner* — Que Tan Le
(74) *Attorney, Agent, or Firm* — Maine Cernota & Rardin

(57) ABSTRACT

An inspection system for visually inspecting one or more inspection locations within a structure, the inspection system including one or more imaging devices mounted within the structure to view the inspection locations, at least one light source to illuminate the inspection locations during inspection, and a wiring harness extending from the imaging device to at least one external port of the structure and configured to supply electrical power to the imaging device from a power supply external to the structure when con-
(Continued)

nected to the port during inspection, and to carry image data representing images of the inspection locations from the imaging device to an external device for viewing by a user of the inspection system.

11 Claims, 1 Drawing Sheet

(51) Int. Cl.
*G01N 21/95* (2006.01)
*G01N 21/954* (2006.01)
*H04N 7/18* (2006.01)
*G01J 1/42* (2006.01)
*G01J 1/44* (2006.01)

(52) U.S. Cl.
CPC ....... *G01N 21/954* (2013.01); *G01N 21/9515* (2013.01); *H04N 7/181* (2013.01)

(58) Field of Classification Search
USPC .................................. 250/559.4, 221, 208.1
See application file for complete search history.

(56) References Cited

U.S. PATENT DOCUMENTS

| | | |
|---|---|---|
| 4,696,544 A | 9/1987 | Costella |
| 4,757,258 A | 7/1988 | Kelly, Jr. et al. |
| 4,795,606 A | 1/1989 | Fenemore et al. |
| 4,816,828 A * | 3/1989 | Feher .................... B64D 43/00 244/1 R |
| 6,847,394 B1 | 1/2005 | Hansen et al. |
| 2002/0104921 A1 | 8/2002 | Louvel |
| 2006/0043303 A1 | 3/2006 | Safai et al. |

OTHER PUBLICATIONS

International Search Report and Written Opinion of International Application No. PCT/AU2016/050049, dated Mar. 11, 2016, 10 pages.
European Search Report for Appl No. 16754665.4 dated Sep. 5, 2018, 7 pages.
European Search Report for Appl No. 16754664.7 dated Sep. 11, 2018, 13 pages.

* cited by examiner

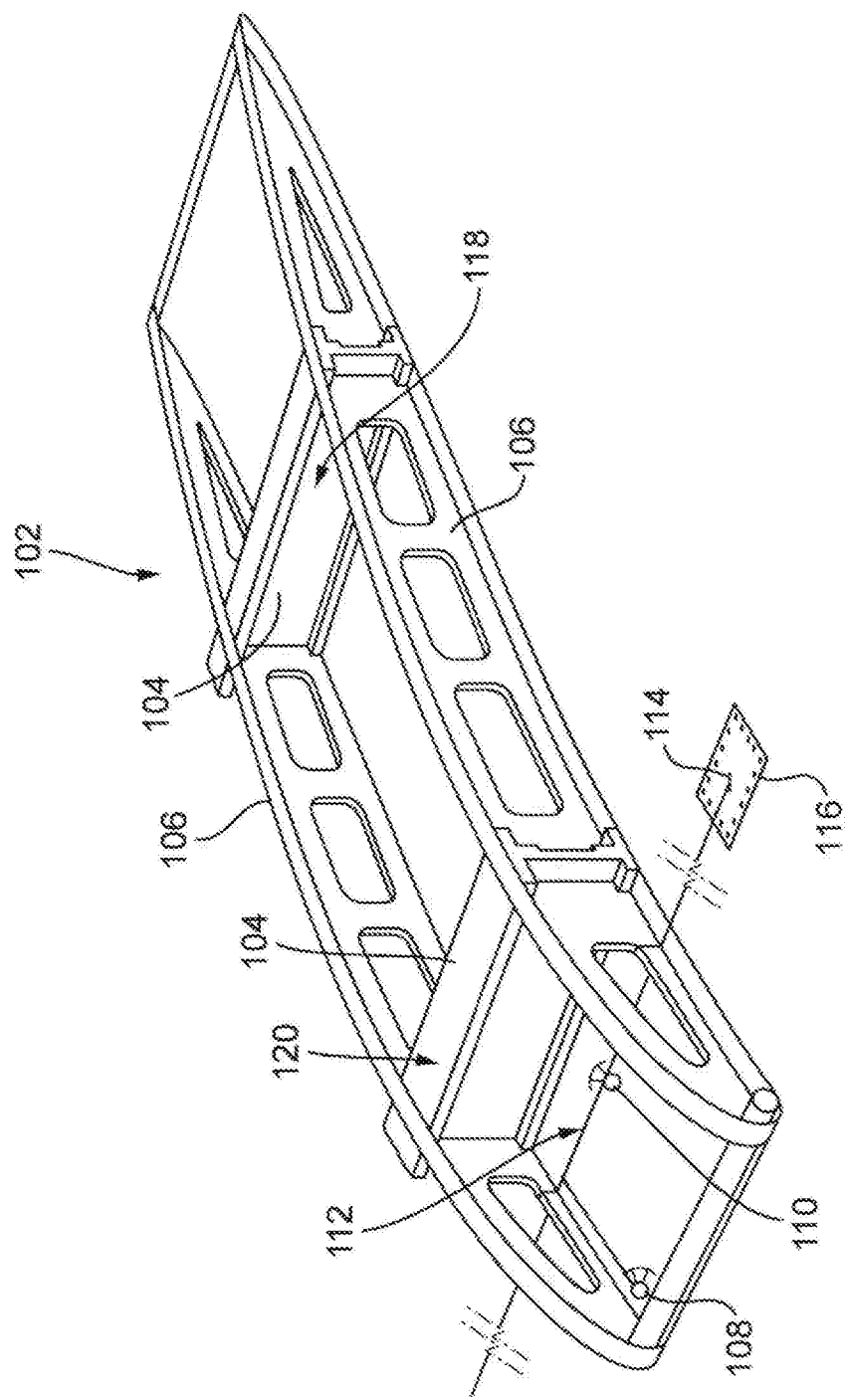

INSPECTION SYSTEM COMPRISING A WIRING HARNESS THAT WHEN CONNECTED TO AN EXTERNAL POWER SUPPLY FOR SUPPLYING ELECTRIC POWER AND IMAGE DATA TO AND FROM AN IMAGING DEVICE MOUNTED WITHIN AN INSPECTED STRUCTURE

RELATED APPLICATIONS

This application is a national phase application filed under 35 USC § 371 of PCT Application No. PCT/AU2016/050050 with an International filing date of Jan. 29, 2016 which claims priority of AU Patent Application 2015900630 filed Feb. 23, 2015. Each of these applications is herein incorporated by reference in its entirety for all purposes.

FIELD OF THE INVENTION

The present invention relates to an inspection system, in particular for inspecting difficult to access locations of or within a structure.

BACKGROUND

There are many situations in which it is important to perform inspections at locations that are difficult or impossible to access directly by a person. For example, such locations may be deep within an apparatus or structure, possibly requiring navigation of a complex or tortuous path, and/or may be within a sealed, enclosed, or otherwise inaccessible enclosure, or may simply be remote from any location directly accessible by a person. Such inspections are not necessarily limited to visual inspections, but and include inspection using any one or more of a wide variety of different types of inspection devices or sensors, typically (but not necessarily) in combination with visual inspection.

For example, preventive maintenance inspections of a structure or apparatus are commonly conducted using a schedule-based inspection regime that is imposed by its manufacturer and/or by a regulatory body. Often this involves disassembling the structure/apparatus, finding nothing, and then reassembling. Such a necessary but fruitless exercise comes at the expense of wasted downtime, wasted inspector time, added cost, and sometimes the accidental production of maintenance-induced damage or faults. Conversely, sometimes it happens that significant and unforseen damage is unexpectedly found during an inspection, leading to extended platform downtime (often exacerbated by lead times for spare parts), higher than expected labour time and costs for repair, and a significant impact on total maintenance resources and operation.

In this regard, the burden of corrosion is becoming increasingly significant across a number of industries due to factors such as increased pressure to extend service life, operations in more severe environments, reduced effectiveness of environmentally-friendly corrosion inhibitors, increased OH&S requirements for access into dangerous spaces, overly rigorous mandated inspection regimes causing maintenance-induced damage, and other causes.

For example, defence forces are becoming increasingly concerned at the increasing cost and platform downtime due to corrosion, and it is not unusual to lose more than 10% of an annual fleet availability due to corrosion. One recent study concluded that aircraft corrosion cost the Australian Defence Force $238 M in 2013. Moreover, maintenance regimes also exist where two-thirds of scheduled inspections are for corrosion, and more damage is done by the resulting disassembly and reassembly of the structure than by actual material oxidation.

However, maintenance inspection is only one reason to inspect difficult to access locations.

It is desired, therefore, to address or alleviate one or more difficulties of the prior art, or to at least provide a useful alternative.

SUMMARY

In accordance with some embodiments of the present invention, there is provided an inspection system for visually inspecting one or more inspection locations within a structure, said inspection system including one or more imaging devices mounted within said structure to view said inspection locations, at least one light source to illuminate said inspection locations during inspection, and a wiring harness extending from the imaging device to at least one external port of the structure and configured to supply electrical power to the imaging device from a power supply external to said structure when connected to said port during inspection, and to carry image data representing images of the inspection locations from the imaging device to an external device for viewing by a user of the inspection system.

In some embodiments, each of said imaging devices including a remotely operable shutter to selectively expose an imaging aperture or lens of the imaging device in order to view said inspection locations during inspection and to protect said imaging lens or aperture at other times, In some embodiments, at least one of said imaging devices is mounted to a corresponding mount or stage that is remotely operable to selectively move and/or orient the imaging device to view said inspection locations during inspection and to move and/or orient the imaging device to a storage position and/or orientation in order to protect said imaging device at other times.

In some embodiments, said one or more inspection locations are within an enclosed cavity of a vessel or vehicle.

In some embodiments, said one or more inspection locations are within a fuselage or wing cavity of an aircraft.

In some embodiments, said at least one light source is configured for illumination at least two of: (i) infra-red, (ii) visible, and (iii) ultraviolet wavelengths.

In accordance with some embodiments of the present invention, there is provided an inspection method for facilitating inspection of one or more relatively inaccessible inspection locations of a structure or second apparatus, said method including mounting one or more imaging devices within said structure to view said inspection locations, at least one light source to illuminate said inspection locations during inspection, and a wiring harness extending from the imaging device to at least one external port of the structure and configured to supply electrical power to the imaging device from a power supply external to said structure when connected to said port during inspection, and to carry image data representing images of the inspection locations from the imaging device to an external device for viewing by a user of the inspection system.

In some embodiments, each of said imaging devices includes a remotely operable shutter to selectively expose an imaging lens or aperture of the imaging device in order to view said inspection locations during inspection and to protect said imaging lens or aperture at other times, In some embodiments, at least one of said imaging devices is mounted to a corresponding mount or stage that is remotely operable to selectively move and/or orient the imaging device to view said inspection locations during inspection and to move and/or orient the imaging device to a storage position and/or orientation in order to protect said imaging device at other times, In some embodiments, said one or more inspection locations are within an enclosed cavity of a vessel or vehicle.

In some embodiments, said one or more inspection locations are within a fuselage or wing cavity of an aircraft.

BRIEF DESCRIPTION OF THE DRAWINGS

Preferred embodiments of the present invention are hereinafter described, by way of example only, with reference to the accompanying drawings, wherein:

FIG. 1 is a schematic diagram illustrating an inspection system installed within a wing section of an aircraft in accordance with an embodiment of the present invention.

DETAILED DESCRIPTION

The described embodiments of the present invention include an inspection system for facilitating the inspection of relatively inaccessible inspection locations of a structure, in particular inspection locations internal to the structure. The inspection system can advantageously be applied to inspect internal inspection locations of a mobile structure, such as a vessel or vehicle.

The inspection system described herein includes a system of imaging devices mounted within a structure that is to be inspected from time to time. The imaging devices are configured to view inspection locations within the structure. In some embodiments, each imaging device includes a remotely operable shutter to selectively expose an imaging lens, aperture, or sensor of the imaging device in order to view the inspection locations during inspection and to protect the imaging lens, aperture, or sensor from contamination or damage at other times. Each imaging device also includes a light source to illuminate the inspection locations during inspection. The light source, lens and/or sensor can advantageously be configured to facilitate imaging at visible, infra-red, and/or ultraviolet wavelengths to provide enhanced or additional information about the condition of the structure.

The inspection system also includes a wiring harness extending from the imaging device to at least one external port of the structure. The wiring harness is configured to supply electrical power to the imaging device from a power supply external to the structure when connected to the port during inspection. The wiring harness also carries image data representing images of the inspection locations from the imaging device to an external device for viewing by a user of the inspection system.

The inspection system is particularly advantageous for use in situations where the cost of inspection is higher than the cost of implementation, such as bays or tanks:

i. that are frequently inspected;
  ii. that are in deep, hidden locations;
  iii. which require costly new fasteners/consumables in reassembly;
  iv. which pose safety risks; and/or
  v. which often suffer maintenance induced damage.

In one embodiment, an inspection system is installed within the wings of an aircraft. FIG. 1 is an illustration of one section 102 of an aircraft wing. As can be seen, each aircraft wing includes fore and aft first structural members or spars 104 running along the span of the wing, and second structural members 106 transverse to the spars 104, these collectively dividing the internal volume of the wing into fore, central, and aft cavities, bays, or 'boxes'. As shown in FIG. 1, first structural members 106 are solid and thus divide each wing section into three mutually isolated bays, whereas the second structural members 106 include openings that allow access from bay to bay along the length of each wing.

In order to monitor the condition of the wing, each cavity or bay can include one or more imaging devices. In the embodiment of FIG. 1, the foremost or front box of the wing section 102 includes two imaging devices 108, 110 (which in some embodiments may be 'digital cameras'), to allow the internal spaces of the wing to be remotely inspected for condition monitoring. In particular, the forward-facing face of the wing spar 104 is typically susceptible to corrosion. Accordingly, one imaging device 108 has a fisheye lens to monitor the general condition of the entire bay (including the wiring harness 116 and the second imaging device 110), and the second imaging device 110 is installed at the base of the spar 104 and is configured with a wide angle lens in order to closely monitor the spar web 118 and spar cap 120 of the spar 104. An additional pair of imaging devices is installed in the same configuration in each of the other front wing boxes (not shown) in order to monitor the condition of those wing boxes.

The inspection systems described herein can provide high definition resolution in extremely compact and light packages. A circular LED array mounted around the lens of the imaging device provides (visible wavelength in this instance) lighting of the inspection locations. The lens configuration of each imaging device 108, 110 is selected based on the imaging device location and desired field of view, and is typically a wide angle or fisheye lens. In general, the optics configuration and output can be tailored to meet the requirements for each location. In some embodiments, each imaging device is equipped with a remotely operable mechanical lens cap or cover that automatically opens when the imaging device is powered and protects the lens when the imaging device is not in use.

In some embodiments, at least one imaging device is mounted on a mount or stage that includes remotely operable stepper motors in order to control the position and/or orientation of the imaging device. This allows the imaging device to selectively view different inspection regions under operator control. Additionally, the imaging device can be positioned and/or oriented to adopt a 'park' or storage position/orientation in order to protect a lens or aperture of the imaging device when the imaging device is not in use. In such embodiments, the imaging device need not include the lens or cover The two imaging devices 108, 110 in the fore bay of the wing section 102 are connected via a common wiring harness 112 to an external electrical connector 114 that is accessible from a wing access port 116 on the underside of the aircraft wing. Other imaging devices (not shown) may be mounted within the central or aft bays of the wing, and, if so, have their own wiring harness(es) connecting them to respective external electrical connectors (not shown), also accessible from the wing access port 116 (or, in some embodiments, a different wing access port).

In order to perform an inspection, a maintenance person takes a mobile power supply and image storage and display device (typically, in the form of a notebook or tablet computer) to the aircraft, and connects these to the wiring harness 112 via the electrical connector located in the wing access port 116. When the mobile power supply is connected, electrical power flows from the power supply to the digital imaging devices 108, 110, which has the effect of booting up each imaging device 108, 110, opening its lens cover (where applicable) or moving/reorienting the imaging device from its storage configuration (where applicable), and powering up its light source. Images acquired by each imaging device 108, 110 are transmitted by each imaging device 108, 110 to the image storage and display device via the wiring harness 112. The received images can be displayed as they are received, allowing the maintenance person to immediately assess any obvious signs of corrosion or other maintenance issues. Additionally, the newly acquired images can be compared with previously acquired images from the same inspection locations, allowing maintenance personnel to more thoroughly assess any changes that have occurred in the interim.

In some embodiments, an inspection is able to be performed remotely, by the maintenance person connecting the wiring harness 112 to an image acquisition device having a wired or wireless network interface connected to a wide area communications network such as the Internet. This allows a structure to be inspected by a person located remotely from the structure. For example, a wind turbine located in the Netherlands can be inspected by a person located in Australia.

As described above, the inspection system is only powered when interfaced with an external power supply via the wiring harness, thus removing the need for installed batteries (or aircraft power, in the case of installation within an aircraft) or a data acquisition and storage unit. The installation is therefore very small, light and poses little, if any, safety concerns.

As will be apparent to those skilled in the art, the imaging devices can be made using commercially available image sensors such as CMOS or CCD image sensors available from companies such as Toshiba or Samsung, amongst others, and associated standard electronic components known to those skilled in the art to receive data from the image sensor and send it to the image storage and display device via a standard communications interface using a standard communications protocol such as USB, for example. Alternatively, in some embodiments, the imaging devices are commercially available digital cameras having USB interfaces, and the wiring harness to each digital camera includes a corresponding USB cable. By way of example, suitable commercially available digital cameras include 'web cams', radio control aeroplane cameras, 'first person view' (FPV), or 'sport action' cameras, and the like. Other suitable types of digital camera will be apparent to those skilled in the art.

In some embodiments, each digital camera is also powered via its USB cable, so that its wiring harness is the USB cable. In embodiments where the electrical power requirements of the digital cameras are sufficiently low, each digital camera can be powered by standard USB power, eliminating the need for an external power supply separate to the image storage and display device (which may be a laptop computer).

The inspection systems described herein provide considerable advantages over manually performed inspections in difficult to access locations. For example, visual inspection by an installed optics system allows easy and frequent monitoring of a structure, rather than infrequent, costly and time-consuming scheduled inspections. Where the inspections includes monitoring for corrosion, and corrosion is detected, the progression of corrosion can be tracked and predicted. The inspection system can also be used to detect precursors to corrosion (e.g., paint degrading/flaking/dulling/powdering, smoking rivets, wetness, etc), so that effective and early preventative action can be taken. If preventative action is unsuccessful or not possible, corrosion initiation can be closely monitored until refurbishment is required, as specified by normal visual inspection processes and standards.

As described above, in some embodiments, the imaging devices/cameras are installed within an aircraft. Corrosion research for aircraft remains predominantly aluminium-centric, whereas new aircraft use increasingly less Al alloy. However, the inspection system can provide monitoring of other increasingly used materials, such as composites, titanium, for aircraft, and enables monitoring for other structures with or without dedicated corrosion research/sensors/models.

The inspection systems described herein can also be used to monitor for blocked drainage holes, swarf, fretting components, airframe cracking, loose avionics connectors, frayed wiring, foreign objects, etc. The inspection systems can therefore collect sufficient trusted data to avoid the need for physical visual inspections, so that the full cost and time benefits of removing inspections is realised.

Many modifications will be apparent to those skilled in the art without departing from the scope of the present invention.

What is claimed is:

1. An inspection system for visually inspecting one or more inspection locations within a structure, said inspection system comprising:
    at least one imaging device mounted within said structure to view said inspection locations;
    at least one light source configured to illuminate said inspection locations during an inspection thereof; and
    a wiring harness extending from the imaging device to at least one external port of the structure and configured to supply electrical power to the imaging device from a power supply external to said structure when connected to said port during inspection, and to carry image data representing images of the inspection locations from the imaging device to an external device that enables viewing of the images by a user of the inspection system.

2. The inspection system of claim 1, wherein each of said imaging devices including a remotely operable shutter configured to selectively expose an imaging aperture or lens of the imaging device so that the imaging device is able to view said inspection locations during said inspection, and to protect said imaging lens or aperture at other times.

3. The inspection system of claim 1, wherein at least one of said imaging devices is mounted to a corresponding mount or stage that is remotely operable to selectively move and/or orient the imaging device so as to enable the imaging device to view said inspection locations during said inspection, and to move and/or orient the imaging device to a storage position and/or orientation in order to protect said imaging device at other times.

4. The inspection system of claim 1, wherein said one or more inspection locations are within an enclosed cavity of a vessel or vehicle.

5. The inspection system of claim 4, wherein said one or more inspection locations are within a fuselage or wing cavity of an aircraft.

6. The inspection system of claim 1, wherein said at least one light source is configured for illumination at at least two of: (i) infra-red, (ii) visible, and (iii) ultraviolet wavelengths.

7. An inspection method for facilitating inspection of one or more inspection locations of a structure, said method comprising:

mounting within said structure one or more imaging devices configured to view said inspection locations mounting within said structure at least one light source configured to illuminate said inspection locations during an inspection; and mounting within said structure a wiring harness extending from the imaging device to at least one external port of the structure and configured to supply electrical power to the imaging device from a power supply external to said structure when connected to said port during said inspection, and to carry image data representing images of the inspection locations from the imaging device to an external device for viewing of the images by a user of the inspection system.

8. The inspection method of claim 7, wherein each of said imaging devices includes a remotely operable shutter configured to selectively expose an imaging lens or aperture of the imaging device so that the imaging device is able to view said inspection locations during said inspection, and to protect said imaging lens or aperture at other times.

9. The inspection method of claim 7, wherein at least one of said imaging devices is mounted to a corresponding mount or stage that is remotely operable to selectively move and/or orient the imaging device so as to enable the imaging device to view said inspection locations during said inspection, and to move and/or orient the imaging device to a storage position and/or orientation in order to protect said imaging device at other times.

10. The inspection method of claim 7, wherein said one or more inspection locations are within an enclosed cavity of a vessel or vehicle.

11. The inspection method of claim 10, wherein said one or more inspection locations are within a fuselage or wing cavity of an aircraft.

* * * * *